United States Patent [19]
Ducheyne et al.

[11] Patent Number: 5,648,301
[45] Date of Patent: Jul. 15, 1997

[54] BIOACTIVE MATERIAL TEMPLATE FOR IN VITRO SYNTHESIS OF BONE TISSUE

[75] Inventors: Paul Ducheyne, Rosemont; Ahmed El-Ghannam; Irving Shapiro, both of Philadelphia, all of Pa.

[73] Assignee: Trustees of the University of Pennsylvania, Philadelphia, Pa.

[21] Appl. No.: 459,002

[22] Filed: Jun. 2, 1995

Related U.S. Application Data

[62] Division of Ser. No. 278,579, Jul. 21, 1994, which is a continuation of Ser. No. 929,104, Aug. 13, 1992, abandoned.

[51] Int. Cl.$^6$ .......................... C03C 3/087; C03C 3/097
[52] U.S. Cl. ................ 501/39; 501/55; 501/63; 501/70
[58] Field of Search .................. 501/39, 55, 63, 501/72, 69, 70

[56] References Cited

U.S. PATENT DOCUMENTS

| | | | |
|---|---|---|---|
| 3,922,155 | 11/1975 | Broemer et al. | 65/33.3 |
| 3,981,736 | 9/1976 | Broemer et al. | 106/39.6 |
| 4,171,544 | 10/1979 | Hench et al. | 3/1.9 |
| 4,605,415 | 8/1986 | Richez | 501/63 |
| 4,608,199 | 8/1986 | Caplan et al. | 530/414 |
| 4,609,551 | 9/1986 | Caplan et al. | 424/95 |
| 4,620,327 | 11/1986 | Caplan et al. | 632/10 |
| 5,204,106 | 4/1993 | Schepers et al. | 424/423 |
| 5,429,996 | 7/1995 | Kaneko | 501/35 |

OTHER PUBLICATIONS

Cheung et al., "Growth of Osteoblasts on Porous Calcium Phosphate Ceramic: An in Vitro Model for Biocompatibility Study", *Biomaterials* 1989, 10, 63–67 No Month.

Cheung et al., "In Vitro Cartilage Formation of Porous Hydroxyapatite Ceramic Granules", *In Vitro Cellular & Developmental Biology* 1985, 21(6), 353–357 No Month.

Davies et al., "Early Extracellular Matrix Synthesis by Bone Cells", Bone–Biomaterials Workshop, editor J.E. Davies, University of Toronto Press, Dec. 1990.

Davies, J.E., ed., "The Bone–Material Interface" in the Preface, University of Toronto Press, 1991 No Month.

Ducheyne et al., "The Effects of Plasma–Sprayed Calcium Phosphate Ceramic Coatings on the Metal Ion Release from Porous Titanium and Cobalt–Chromium Alloys", *J. of Biomedical Materials Res.* 1988, 22, 1137–1163 No Month.

(List continued on next page.)

Primary Examiner—Mark L. Bell
Assistant Examiner—Louis M. Troilo
Attorney, Agent, or Firm—Woodcock Washburn Kurtz Mackiewicz & Norris

[57] ABSTRACT

Novel non-crystalline, porous bioactive glass and ceramic materials that permit the in vitro formation of bone tissue when exposed to a tissue culture medium and inoculated with cells are disclosed. The present invention also discloses methods of treating bioactive glass materials to control pH so that when the glass is exposed to a tissue culture medium and then inoculated with cells, bone tissue growth occurs in vitro. The glass material disclosed is preferably formed from $SiO_2$, $CaO$, $Na_2O$ and $P_2O_5$ and the porous, non-crystalline structure is most preferably created by melting the constituents, cooling and pulverizing the resulting glass, and then forming and hot pressing the powder. The glass of the present invention may be formed to produce templates that are useful for various indications, as well as granules that may be formed into a paste.

5 Claims, 1 Drawing Shee

OTHER PUBLICATIONS

Ducheyne, P., "Bioglass Coatings and Bioglass Composites as Implant Materials", *J. of Biomedical Materials Res.* 1985, 19, 273–291 No Month.

Freshney et al., "Animal Cell Culture a Practical Approach", Freshney, R.I., ed., IRL Press, Oxford, 1986 No Month.

Greenlee et al., "Glass–Ceramic Bone Implants", *J. Biomedical Materials Res.* 1972, 6, 235–244 No Month.

Gregoire et al., "The Influence of Calcium Phosphate Biomaterials on Human Bone Cell Activities: An In Vitro Approach", *J. Biomed. Mat. Res.* 1990, 24, 165–177 No Month.

Gross, U. and Strunz, "The Interface of Various Glasses and Glass Ceramics with a Bony Implantation Bed", *J. of Biomed. Materials Res.* 1985, 19, 251–271 No Month.

Hench et al., "Bonding Mechanisms at the Interface of Ceramic Prosthetic Materials", *J. Biomed. Mat. Res.* 1972, 2, 117–141 No Month.

Katsufumi et al., "The Influence of Calcium Phosphate Ceramics and Glass Ceramics on Cultured Cells and Their Surrounding Media", *J. Biomed. Mat. Res.* 1989, 23, 1049–1066 No Month.

Kim et al., "Early Stages of Calcium Phosphate Layer Formation in Bioglass", *J. Non.–Cryst. Solids.* 1989, 113, 195–202 No Month.

Koeneman et al., "Workshop on Characterization of Calcium Phosphate Materials", *J. of Applied Biomaterials* 1990, 1, 79–90 No Month.

Kokubo et al., "Solutions Able to Reproduce In Vivo Surface–Structure Changes in Bioactive Glass–Ceramic A–W$^3$", *J. Biomed. Mat. Res.* 1990, 24, 721–734 No Month.

Kokubo, T. et al., "Ca, P–rich Layer Formed on High–strength Bioactive Glass–ceramic A–W", *J. of Biomed. Mat. Res.* 1990, 24, 331–343 No Month.

Lowenberg et al., "Mineralized Matrix Production by Osteoblasts on Solid Titanium in Vitro", *Cells & Materials* 1991, 1(2), 177–187 No Month.

Lowry et al., "The Quantitative Histochemistry of the Brain. II. Enzyme Measurements", *J. Biol. Chem.* 1954, 207, 19–37 No Month.

Maniatopoulos et al., "Bone Formation in Vitro by Stromal Cells Obtained from Bone Marrow of Young Adult Rats", *Cell Tissue Res.* 1988, 254, 317–330 No Month.

Matsuda et al., "The In Vitro Response of Osteoblasts to Bioactive Glass", *Biomaterials* 1987, 8, 275–284 No Month.

Ohgushi et al., "Osteogenic Capacity of Rat and Human Marrow Cells in Porous Ceramics", *Acta Orthop. Scand.* 1990, 61(5), 431–434 No Month.

Ohgushi et al., "Heterotopic Osteogenesis in Porous Ceramics Induced by Marrow Cells", *J. Ortho. Res.* 1989, 7, 568–578 No Month.

Ohtsuki, C. et al., "Apatite Formation on the Surface of Ceravital–type Glass–ceramic in the Body", *J. of Biomedical Materials Res.* 1991, 25, 1363–1370 No Month.

Orly et al., "Effect of Synthetic Calcium Phosphate on the $^3$–Thymidine Incorporation and Alkaline Phosphatase Activity of Human Fibroblasts in Culture", *J. Biomed. Mat. Res.* 1989, 23, 1433–1440 No Month.

Puleo et al., "Osteoblast Responses to Orthopaedic Implant Materials in Vitro", *J. Biomed. Mat. Res.* 1991, 25, 711–723 No Month.

Schepers et al., "Bioactive Glass Particles of Narrow Size Range: A New Material for the Repair of Bone Defects", *Implant Dent.* 1993, 2, 151–156 No Month.

Schepers et al., "Bioactive Glass Particulate Material as a Filler for Bone Lesions", *J. Oral Rehabilitation* 1991, 8, 435–452 No Month.

Uchida et al., "Growth of Bone Marrow Cells on Porous Ceramics in Vitro", *J. Biomed. Mat. Res.* 1987, 21, 1–10 No Month.

Vrouwenvelder et al., "Better Histology and Biochemistry for Osteoblasts Cultured on Titanium–Doped Bioactive Glass: Bioglass 45S5 Compared with Iron–, Titanium–, Fluorin– and Boron–Containing Bioactive Glasses", *Biomaterials* 1994, 15, 97–110 No Month.

Vrouwwenvelder et al., "Behaviour of Fetal Rat Osteoblasts Cultured IN Vitro on Bioactive Glass and Nonreaactive Glasses", *Biomaterials* 1992, 13(6), 382–392 No Month.

Vrouwenvelder et al., "Histological and Biochemical Evaluation of Osteoblasts, Cultured on Bioactive Glass, Hydroxylapatite, Titanium Alloy, and Stainless Steel", *J. Biomed. Mat. Res.* 1993, 27, 465–475 No Month.

Pernot et al. "Phosphate Glass–Ceramic for Bone Implants," in Ceramics in Surgery, edited by P. Vincenzini, Elsevier, Amsterdam 1983 pp. 177–186.

BIOACTIVE MATERIAL TEMPLATE FOR IN VITRO SYNTHESIS OF BONE TISSUE

This is a division of application Ser. No. 08/278,579, filed on Jul. 21, 1994, which is a Rule §1.62 FWC of Ser. No. 07/929,104; filed on Aug. 13, 1992, now abandoned.

The present invention relates to the synthesis of bioactive ceramic templates for optimum in vitro formation of bone and bone-like tissue. The fundamental mechanisms by which material surfaces elicit the in vitro response from bone cells are optimized, thereby leading to high formation rates of extracellular material with typical characteristics of bone tissue.

BACKGROUND OF THE INVENTION

Materials were first used to provide structural support during healing of bones, or to replace damaged or diseased bone tissue. Historically, the most important material selection criterion was inertness. It was believed that the implant material should only provoke the slightest reactions in the body. It is important to realize, though, that no matter how chemically inert a material may be, it always provokes a reaction upon implantation. The intensity of the reaction depends not only on the surface and bulk properties of the implant material, but also on the trauma at the time of surgery, the site of implantation, and the relative motion at the tissue-implant interface. This observation has prompted the use of "bioactive" materials instead of so-called inert materials. The implication is that a bioactive material must provoke a beneficial tissue response, specifically it must elicit the formation of the normal tissue at its surface and create an interface that promotes long functional life. Whereas the field of calcified tissue reconstruction has achieved this goal, this advance is not an end state, but merely a stepping stone for an even more ambitious goal: the creation of materials that are capable of serving as templates for in vitro bone tissue formation. This is part of the true future of biomaterials: creating materials that, once inserted into the body, regenerate tissues rather than replace them.

Cell culture studies with osteoprogenitor cells or cells of osteoblastic phenotype have been performed, but never achieved acceptable results. Some of these prior studies did not seek the optimization per se of extracellular material synthesis. Some prior studies used osteoprogenitor cells present in bone marrow extracts. Regardless of whether focus is placed on the determination of osteoblastic phenotype expression or elsewhere, these results can be used to determine whether one of the resultant phenomena of osteoblastic phenotypic activity was extensive or not.

It is known to obtain bone marrow cells from the femora of young adult male Wistar rats by washing them out with α MEM (minimal essential medium) supplemented with 15% fetal bovine serum, freshly prepared ascorbic acid, sodium β-glycerophosphate, dexamethasone (DEX) and antibiotics. See, Davies et al. "Early extracellular matrix synthesis by bone cells," Bone-Biomaterials Workshop, J. E. Davies Ed., University of Toronto Press, (December 1990). A quantity of this cell suspension, e.g., 30 ml, containing cells from two femora, is aliquoted on to the material substrate. In a humidified 95% air −5% $CO_2$ atmosphere the culture is maintained for a minimum of two weeks. It was shown that a calcified matrix of globular accretions, also containing sulphur, is formed. This layer was typical for reversal lines in bone tissue, the cementum layer, and was considered by the authors as evidence that the calcified layer is the result of the expression of the osteoblastic phenotype by the cultured cells. Subsequently, there was what was called "frank bone formation." Thus, matrix production can start within a time period of intermediate duration (17 days) by differentiating bone-derived cells in vitro. It has also been reported, however, that no calcified tissue formation has been obtained on porous ceramics. See Uchida et al. "Growth of bone marrow cells on porous ceramics in vitro," J. Biomed, Mat. Res. 21:1–10 (1987). The observation in the prior art with respect to the intrinsic capability of cells to deposit a cement-like line is in any event certainly correct. The cell culture method described above is derived form Maniatopulos et al.'s "Bone formation in vitro by stromal cells obtained from bone marrow of young adult rats," Cell Tissue Res. 254:317–330 (1988), wherein this particular cellular activity was shown to be present in cultures without any tissue stimulating biomaterial.

The effect of porous calcium phosphate ceramic on growth and hormonal response of periosteal fibroblasts, osteoblasts, and chondrocytes has been disclosed by other workers. See, e.g., Cheng et al., "Growth of osteoblasts on porous calcium phosphate ceramic: an in vitro model for biocompatibility study," Biomaterials, 10, 63–67 (1989). As reported in this reference, the number of these cells increased 29-, 23- and 17-fold during a ten week time period. Osteoblasts retained their phenotypic expression by producing only Type I collagens. Previously, Cheng had shown that the phenotypic expression of canine chondrocytes had been retained up to 13 months when cultured on porous hydroxyapatite ceramic granules. See Cheng, "In vitro cartilage formation on porous hydroxyapatite ceramic granules," In Vitro Cellular & Developmental Biology, 21:6, 353–357 (1985). The elaboration of extracellular matrix reportedly started to appear at week one and increased throughout a thirteen month period.

Still others have studied the attachment and subsequent growth of V79 cells in contact with various calcium phosphate ceramics and found that cell growth was markedly inhibited by hydroxyapatite, and slightly inhibited by tricalcium phosphate and glass ceramics. See Katsufumi et al., "The influence of calcium phosphate ceramics and glass ceramic on cultured cells and their surrounding media," J. Biomed Mat. Res., 24:1049–1066 (1989). Under conditions of phagocytosis of small bioactive ceramic powders, RNA transcription and protein synthesis of osteoblast populations have been stimulated. See Gregoire et al. "The influence of calcium phosphate biomaterials on human bone cell activities: An in vitro approach," J. Biomed Mat. Res. 24:165–177 (1990). This phenomenon has also been observed for phagocytosing fibroblasts. It has been suggested that the increase of $^3$H-thymidine incorporation into DNA and the decrease of alkaline phosphatase activity probably resulted from secondary calcium messenger pathways. See Orly et al. "Effect of synthetic calcium phosphate on the $^3$H-thymidine incorporation and alkaline phosphatase activity of human fibroblasts in culture," J. Biomed Mat. Res. 23:1433–1440 (1989). Another study by Puleo et al., "Osteoblast responses to orthopaedic implant materials in vitro," J. Biomed Mat. Res. 25:711–723 (1991), provided inconclusive results regarding osteoblast attachment, osteoblast proliferation and collagen-synthesis.

Another set of studies performed in vivo, documenting materials-dependent tissue response patterns are noteworthy. A series of experiments with porous hydroxyapatite and bone marrow cells was started by Ohgushi, Goldberg and Caplan and subsequently continued separately by Ohgushi and associates in Nara, Japan and Caplan and associates in Cleveland, Ohio (USA). See Ohgushi et al. "Heterotopic osteogenesis in porous ceramics induced by marrow cells," J. Ortho. Res., 7:568–578 (1989). These experiments demonstrate that the osteoprogenitor nature of the cells of a marrow cell suspension, implanted in heterotopic sites, are activated more readily when the suspension is infused into porous hydroxyapatite than when implanted by itself.

Finally, U.S. Pat. No. 4,609,501—Caplan et al. discloses the stimulation of bone growth that includes the in vitro exposure of isogenic fibroblasts to a soluble bone protein capable of stimulating a chondrogenic response. The exposed cells are combined with a biodegradable carrier such as fibrin, although it is also suggested that the exposed cells may also be incubated with a prosthesis. A related Caplan et al. patent, U.S. Pat. No. 4,609,551, discloses techniques for delivering the bone protein to anatomical sites, while U.S. Pat. No. 4,608,199 also to Caplan et al. discloses processes for obtaining suitable bone protein.

The present invention is focused on substrate materials and shows that modification of the material used as the substrate can lead to major differences in amount and rate of tissue formation in vitro. It is thus an object of this invention to synthesize ceramic materials which serve as the ideal templates upon which life processes, specifically, bone tissue formation, can thrive.

SUMMARY OF THE INVENTION

These and other objects are met by the synthesis of porous glass without producing significant crystallization and the conditioning of the glass surface such that cell attachment is enhanced and extensive extracellular matrix (ECM) formation can take place. Control of the bioactivity reactions to produce pH variation in solution within boundaries that do not kill the cells once seeded on the porous glass is also disclosed.

Generally, the present invention discloses a bioactive material surface treated to enhance bone cell attachment and activity when the material is placed in a tissue culture medium, such that when inoculated with cells, bone tissue forms in vitro. Preferably, the bioactive comprises a glass treated to control pH, most preferably to less than 7.6. In a preferred embodiment, the bioactive material is a non-crystalline glass consisting essentially of: $SiO_2$; $CaO$; $Na_2O$; and $P_2O_5$ having the following preferred composition: 45% by weight $SiO_2$; 24.5% by weight $CaO$; 24.5% by weight $Na_2O$; and 6% by weight $P_2O_5$. Alternatively, in other preferred embodiments, the bioactive material of the present invention comprises a ceramic. In either glass or ceramic forms, however, the material is preferably porous, and the porosity is between 10–80% about 20–30% and the pore size range is less than 800 μm, preferably about 75–200 μm.

The present invention therefore discloses methods of forming a porous glass substrate comprising the steps of melting an admixture consisting essentially of $SiO_2$, $Na_2O$, $CaO$ and $P_2O_5$ and then quenching the melted admixture to create a glass frit. A glass powder is formed from the glass frit that preferably has a particle size between about 40 to 70 μm. A porous glass substrate is then formed from this powder by a foaming process. An important aspect of the present invention is that the resulting porous glass exhibits substantially no crystallization. Crystallization can occasionally be acceptable, but its main drawbacks are the nonuniform corrosion rates of the surface, and therefore the spatial variation of the reaction layers. Furthermore, the corrosion reactions are considerably slower, thereby necessitating long conditioning and incubation times. Alternatively, the porous glass substrate can be formed by creating a slurry of glass powder and a binder such as polyvinyl alcohol and pouring the slurry into a mold, drying the slurry and sintering it to produce a porous glass substrate. Finally, the porous glass substrate can be formed by first quenching the admixture so that a glass is formed. This glass is transformed into a glass ceramic having more than one crystalline phase and then preferentially dissolved to result in a porous material. The preferential dissolution may be accomplished by, for example, adding a solvent such as an acid or a base.

The present invention thus discloses the formation of a porous, preferably non-crystalline, bioactive glass. It is anticipated, though, that any known bioactive glass or ceramic can suitably be transformed to become a template for in vitro synthesis of bone tissue. Inoculation times will probably differ substantially. The glass material disclosed herein can be formed into a prosthetic article such as a disk, a sleeve, a rod or any other form of substrate or template. Alternatively, the glass formed herein can be provided in the form of particles.

In order to enhance bioactivity and bone formation using the glass of the present invention, the glass must be treated to prepare its surface for cell attachment and to control pH prior to its inoculation with cells. Therefore, the present invention also discloses methods of forming bone tissue comprising the steps of providing a porous bioactive template consisting of the glass material described above, immersing the template in a buffer solution and immersing the template in a tissue culture medium to produce a surface which significantly enhances bone cell activity when cells are inoculated on this surface. Finally the template is inoculated with cells and bone tissue is permitted to form thereon. Most preferably, the buffer solution is buffered at a pH of about 6.8 and the tissue culture medium has a pH not exceeding about 7.6. The cells inoculated on the template may be chosen from any preparation providing osteoprogenitor cells, bone marrow cell preparations, cells of osteoblastic phenotypic potential or of osteoblastic phenotype. Inoculation may also proceed with fibroblasts and chondrocytes.

DETAILED DESCRIPTION OF THE INVENTION

Figure 1:
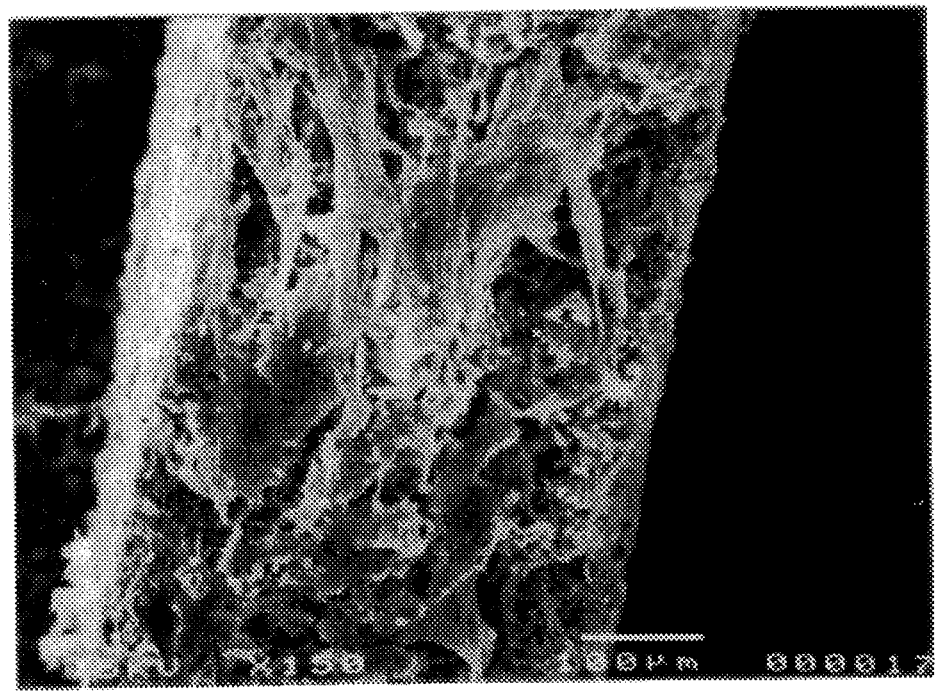
FIG. 1 is a photomicrograph of a cross-section of a substrate made in accordance with the present invention illustrating the formation of bone-like sheets.

In the field of in vivo bone growth, glasses are known to produce a beneficial effect beyond what calcium phosphate ceramics produce. See e.g. Schepers et al. "Bioactive glass particulate material as a filler for bone lesions," J. Oral Rehabilitation, 8, 435–452 (1991). However, this effect in vivo has not been reproduced in vitro. The present invention discloses a new physical form of glass along with an additional new surface treatment that is effective in vitro.

Although porosity of a substrate is not essential, it is advantageous in view of the large specific surface area in potential contact with cells. The growth of tissue through the substrate leads to a fast formation of tissue needed for reimplantation and the artificial material degrades faster. One aspect of the present invention therefore provides methods for making bioactive glass porous. It will be realized that the methods as proposed in the prior art would have produced a crystallized glass, and crystallization must be avoided since it interferes with bioactivity reactions. In other words, the dissolution and ion exchange reactions leading to a calcium-phosphate surface, possibly a carbonated calcium-deficient hydroxyapatite very similar to the mineral phase of bone, are slowed down substantially with crystals being present in the glass. In the limit, it is possible that the necessary calcium-phosphorus rich layer would be formed so slowly that it is of minimal or no consequence to the cellular attachment reaction. If cellular attachment is not achieved, it can be assumed that cellular function will be hampered, if not impeded. Thus, when specifically focusing on the secretory function, that is the extracellular matrix formation or the bone tissue-like synthesis, it would be severely reduced and, therefore, no true utility would be achieved. It should be noted at the outset that the present invention does not rely on cell biology. Many cells that have the potential to be upregulated to cells of the osteoblastic phenotype can be used.

A. GLASS PREPARATION

Bioactive glass with a nominal composition (% by weight) 45% $SiO_2$, 24.5% $Na_2O$, 24.5% CaO and 6% $P_2O_5$ represents a most preferred embodiment and is prepared from chemically pure reagent grade $Na_2CO_3$, $CaCO_3$, $Ca_{10}(OH)_2(PO_4)_6$ and $SiO_2$. However, the following ranges of these constituents are useful to form the material of the present invention: 40–60% $SiO_2$; 5–30% $Na_2O$; 10–35% CaO and 0–12% $P_2O_5$. The prorated amounts of the reagents are admixed and melted in a crucible at about 1350 C. The homogeneity of the melt is assured by swirling the melt-containing crucible as required, but most preferably at least three times. The melt is then poured into deionized water. The glass frit obtained by this method is then dried and used for the synthesis of porous glass. For the synthesis of porous glass, the glass frit is crushed and ground into a powder with a particle size in the range of about 40–70 μm. This powder is admixed with 2–3% $CaCO_3$, which is used as foaming agent. The mixture is hot pressed in vacuum at about 50 MPa and 460 C for about two hours. The resulting pore size range is about 70–200 μm. A larger pore size range, e.g., about 200–500 μm, is obtained by using either $CaCO_3$ powder of a larger particle size, or by using $NaHCO_3$ as the foaming agent. The average porosity and pore size is determined by weight measurements and stereometry, respectively. An X-ray diffraction analysis of porous bioglass prepared in accordance with the present invention shows complete vitrification with no sign of crystallization after the foaming process.

In order to optimize the synthesis of glass in accordance with the present invention, several foaming agents ($Na_2CO_3$, $NaHCO_3$, $NH_4H_2PO_4$ and marble) with different concentrations (1%, 2%, 3%, 6% and 10%) and a number of sintering and foaming treatments (at 450, 580, 475 and 550 C) for different periods of time (1, 2, 3, and 5 hours) were used. Double stage heat treatment (450 C for 1 hr; then heated at either 475 C, 550 C, or 580 C for 1 hr) was also used. Glass powder of different grain sizes, e.g., about 110 μm and between about 70 - 40 μm were used and the applied pressure was also taken as a variable and pressures of about 100, 70, and 40 MPa were tried. Those foaming agents and processing conditions that did not measurably initiate a glass crystallization reaction are preferred. Any crystallization renders glass more corrosion resistant or produces a non-uniform corrosion. This must be avoided as it adversely affects the beneficial formation of the surface reaction layers.

The best result was obtained by admixing the glass powder of grain size between about 40 and 70 μm with about 2.3% $CaCO_3$ that is pressed in a graphite die at a pressure of about 50 MPa. The pressed admixture is then heated at about 460 C for about two hours in a vacuum press. Using high pressure, e.g., about 100 MPa and heat treatment at about 580 C produces non-porous glass-ceramic material, so these values for these variables are not preferred. Moreover, it was found that using low pressure, e.g., about 40 MPa, produces a fragile material that can not be handled. Heat treatment of long duration will initiate crystallization of the glass, especially in the presence of a foaming agent, so the shortest heat treatment duration represents a most preferred embodiment.

Alternative processes useful with the present invention to produce porous glass, glass-ceramic, or ceramic are:

(1) Foaming and Sintering

By making an aqueous ceramic slurry with a binder (e.g., polyvinyl alcohol), and then mixing the slurry with a foaming agent (e.g., $H_2O_2$ or $CaCO_3$) pouring the mixture into a mold, allowing it to dry, and then sintering it at high temperature useful material may be produced. This method is less preferred because it can change the nature of the glass surface and hence limit the bioactivity.

(2) Ceramization and Leaching

By crystallizing the glass into more than one crystalline phase, and then treating the obtained glass ceramic with acid or base that preferentially dissolves one phase and leaves the others, porous material is created. The ceramization and leaching process represents a less preferred embodiment, however, because leaching of calcium phosphate-rich phase will decrease the bioactivity of the glass.

(3) Sol Gel Method

As well known in the art, controlling the heat treatment cycle of the ceramic or glass gel controls the pores and interpores of the material and thus a porous ceramic can be obtained. However, the control of pore size and porosity percent of bioactive glass prepared by this method is much more difficult to obtain in the desirable range than sintering and foaming process described above.

B. CONDITIONING OF THE GLASS SURFACE AND CONTROL OF pH VARIATION

Another important aspect of the present invention is the conditioning of the glass surface with concurrent pH control of the solution. Such conditioning is essential for two reasons: (1) if cells are added to unconditioned glass, the glass corrosion reaction which takes place would lead to pH values at the surface of the glass and in the bulk of the solution that would kill the cells; and (2) the treatment must make the surface ready for expedient cell attachment and extracellular matrix deposition. Before describing the best conditioning of the glass we first describe in a chronological fashion, some of the experiments performed.

Glass disks made in accordance with the techniques described above were soaked in tris buffer solution containing ions in a concentration similar to that found in interstitial fluid, and shaken on a rotary table at 37 C (pH 6.84) for 48 hours. The volume of this solution was one liter. No change in the pH value was measured during the time period of glass immersion. Electron dispersive X-ray analysis (EDXA) revealed that a calcium phosphate rich layer had formed on the surface of the bioactive glass.

In another experiment, the glass disks were either treated in modified tris buffer solution for 20 hours, or treated for 20 hours in tris buffer followed by 48 hours in a typical tissue culture medium (TCM), i.e. E-MEM (Eagles' minimal essential medium +10% NBS +2 mM L- glutamine)

(treatment TB2-E-MEM), then inoculated with cells. Four or five disks were immersed. The solution was maintained at 37 C. A pronounced difference was observed in number of cells attached to the glass disks and secretion of extracellular matrix material. Comparison of the number of cells attached to these two differently treated glasses showed more cells adhered to the glass disks treated in tris buffer alone. Both sets of samples showed collagen fibrils and calcified nodules, yet, neither showed any bone-like tissue formation. The cells attached to the glass disks treated according to TB2-E-MEM produced more collagen fibrils in between the cells. Since cell attachment represents a preferred embodiment, in our subsequent experiments we now assumed that immersion in the modified tris solution was preferable. In this next set of experiments we then addressed the question whether, if we inoculated cells on these disks after treatment in modified tris for 20 hours, there would be a pH variation with the potential of killing of the cells. In these experiments we treated the disks for 20 hours in modified tris and subsequently immersed the disks in the same tissue culture medium as we would use for the inoculation and incubation of cells and we measured the pH variation. We did this first for one ratio of the tissue culture medium volume to glass weight. Thus, we treated glass disks in tris buffer at 37 C for 20 hours followed by immersion in a E-MEM at 37 C. The ratio of solution volume to glass weight was about 19 ml/g. The corrosion products of the glass were found to increase the pH of the TCM solution from 7.6 to 7.9 after 24 hours, and from 7.6 to 8.0 after 48 hours. This increase in pH may have an adverse effect on cells if they were inoculated in such solution, i.e., the cells would die.

A next series of experiments used different ratios of TCM volume to glass weight. Based on the results of the last experiment, we also increased the duration of immersion in tris from 20 to 48 hours. This was intended to minimize subsequent dissolution from the glass into the TCM, when cells would be present. As before, there was a two step immersion: immersion in modified tris buffer solution for 48 hours, and then immersion in TCM for three days. The initial pH of the TCM is 7.6. The pH of the TCM was measured after 24, 48, and 72 hours. The TCM was then replaced by TCM +3 mM B-glycerol phosphate, and the pH was also measured every 24 hours for 3 days. The minimum TCM volume/glass weight ratio that did not change the pH value of the TCM was 90 ml/g, yet there may still be a pH gradient between the glass surface and the bulk of the TCM. Furthermore, the pH value of the TCM inside the pores may be considerably higher than the one of the TCM in the bulk of the solution in the dish. We found that when the pH of the bulk TCM raised to about 7.85, for example, due to a low ratio of TCM volume to glass weight, the activity of the cells that were seeded on the preconditioned glass disks was greatly inhibited. Scanning election microscope (SEM) analysis of these cultures showed very limited cell processes and the alkaline phosphatase activity was minimal, as followed from the faint pink color seen when samples were stained with fast red staining.

Based on the these last results, we performed yet another experiment in which we now added a strong biological buffer to the tissue culture medium: we added 20 mM Hepes. We added this buffer in order to stabilize the pH value inside the pores. Thus, the total set of conditions was: immersion for 48 hours in modified tris, immersion in E-MEM complemented with 20 mM Hepes and a 90 ml/g ratio of TCM volume to glass weight. The second immersion, then, represents conditions for inoculation. Thus, when the pH in the pores and at the surface of the glass was stabilized at 7.6 during the period the cells were seeded on the glass, abundant cell processes were possible and bone like tissue formed extensively after only one week in culture.

The glass disks are dried, and most preferably sterilized by ethylene oxide prior to inoculation with cells.

The effect of the immersion treatment being the formation of calcium phosphate rich reaction layer is known. See Hench et al. "Bonding mechanisms at the interface of ceramic prosthetic materials," J. Biomed. Mater. Res. Symp., 2:117–141 (1972). This reaction layer gradually matures into a poorly crystallized, defective calcium hydroxyapatite structure. See Kim et al. "Early stages of calcium phosphate layer formation in bioglass," J. Non-Cryst. Solids, 113:195–202 (1989). The immersion treatment of the present invention, however, differs in a fundamental way from the method used by Hench et al., referenced above. The intent of the prior art was to establish kinetics of the several ion exchange, dissolution, condensation, precipitation and transformation reactions at the glass surface. For these reasons, a tris-buffered solution which does not contain any of the typical components of interstitial bone fluid was used. In contradistinction, the present invention achieves a glass surface resembling the mineral phase of bone upon which biomolecules are absorbed as soon as the glass is brought into contact with a solution containing biological molecules. This can be achieved by either of two ways: i) prior to inoculation but after immersion in modified tris buffer, the disks are immersed in TCM or any other suitable solution containing biological molecules normally occurring in bone tissue; or ii) the disks are immersed in the cell suspension containing biological molecules. Before the cells adhere, the biological molecules attach to the glass surface and incorporate into the continuously developing glass surface reaction layer. The result is that the developing calcium phosphate layer is coated and intimately mixed with organic molecules.

C. CHARACTERIZATION OF IN VITRO SYNTHESIZED BONE TISSUE

After the above described modified tris buffer pretreatment, the 10 mm diameter disks are placed in 60 mm diameter petri dishes or other suitable container, wetted with TCM and inoculated with about one million neonatal rat calvaria osteoblasts from a suspension containing 1.2 million cells/ml. The cell suspension used herein was obtained by an enzymatic digestion method using 0.2% collagenase. To allow for cell attachment, the petri dishes were kept in the incubator for about one hour prior to flooding them with TCM. Two days later, the TCM was exchanged by TCM supplemented with 3 mM β-Glycerol phosphate. This exchange was repeated at day four. The dishes were sacrificed at day seven. Morphological analysis by using scanning electron microscopy (SEM), energy dispersive x-ray microanalysis (EDXA) for calcium, phosphorus and sulfur, qualitative and quantitative determination of alkaline phosphatase concentration in solution, and DNA, collagen I and osteocalcin synthesis reveal the properties of the tissue that had formed.

Figure 2:
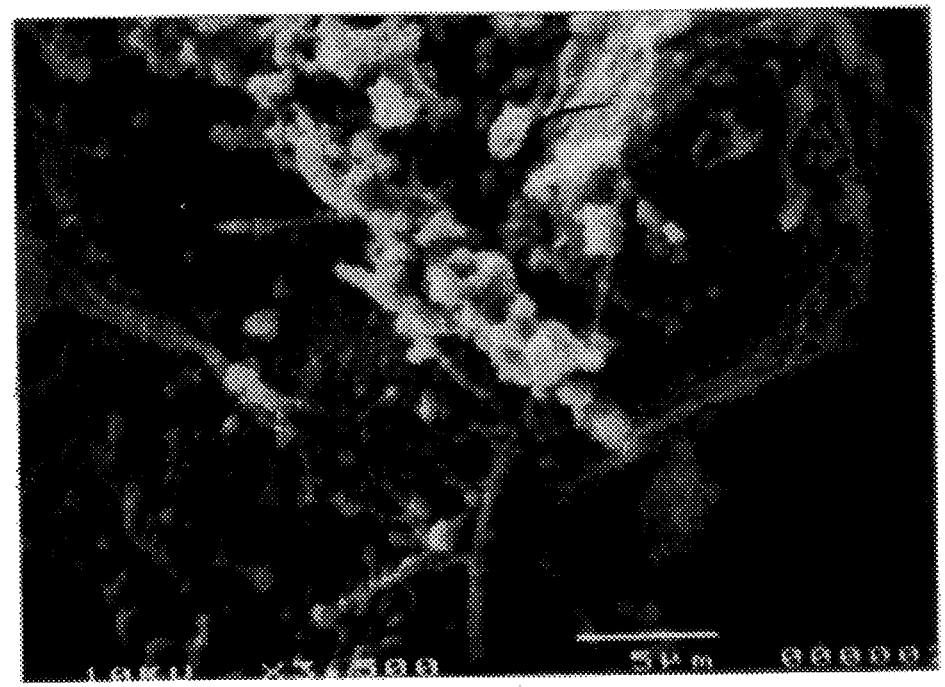
FIG. 2 is a photomicrograph of the surface of bioactive glass made in accordance with the present invention showing globular accretions connected by collagen fibrils.

The porous specimens were found to be totally invaded by the cells and the extracellular matrix they elaborated, as seen in FIG. 1. FIG. 1 shows a scanning electron micrograph (×100) of a cross-section through the porous bioactive glass after 1 week of incubation. Bone-like sheets were formed throughout the whole thickness of the porous glass sample. FIG. 2 shows another scanning electron micrograph (×3500) of the bioactive glass surface. The photograph was made at a time the parameters of our invention were not yet optimized. It shows some of the events prior to the extensive bone tissue formation: globular accretions in direct contact with the glass surface are visible. Collagen fibrils interdigitate with these globular nodules. The calcified cement-like layer is not yet covered by the bone-like sheets and is thus still visible.

The qualitative assessment of alkaline phosphatase activity reveals that the highest activity is with the cells on the bioactive glass disks; there is only a faint activity on the bottom of the petri dishes around the glass disk.

The quantitative determination of the alkaline phosphatase activity expresses an average per dish. Using the method of quantifying released para-nitrophenol (PNP) set forth in Lowry et al. "The quantitative histochemistry of the brain: II. Enzyme measurements," J. Biol Chem., 207:19–37 (1954), a rate of 0.62 nmol pNP/min/µg protein was found. As for µg DNA, a typical value (2.01 µg/ml) for osteoblastic phenotypic expression was indicated. The extensive morphologic observation of the various samples suggests the following hypothetical sequence of events: in a first step the foci of calcification form: small globules, 1–2 µm in diameter, appear on the glass surface. Subsequently, collagen fibrils are produced and attach to the calcified nodules.

It should be noted that collagen I synthesis has been confirmed. From thereon, the synthesis of both calcified substance and intertwined fibrils continues, thereby leading to the gradual formation of bundles and eventually the coalescence into sheets of bone-like material. It is important to note that the surface of these sheets is smooth and free of calcified globules. Such observations are intriguing as they fit the theory that these calcified globules serve to bridge the collagen fibrils and thereby create the continuous bone-like sheets. It is another intriguing observation that without the initial elaboration of these nodules on the glass surface, the cells do not produce collagen fibrils. Osteocalcin radioimmunoassay (using goat anti-rat osteocalcin, donkey anti-goat second antibody and I-125 rat osteocalcin) showed a considerable concentration (about 8 ng/ml) of osteocalcin. Osteocalcin was detected only on those dishes containing glass and osteoblasts. Control dishes with osteoblasts but without glass disks never showed appreciable concentration of osteocalcin.

The calcification of elaborated material was not the result of a physio-chemical phenomenon of precipitation from a solution supersaturated in calcium and phosphorus, this in itself resulting from glass dissolution. Control experiments with glass without inoculation of cells, or cell culture experiments without porous bioactive glass did not produce a measurable calcification.

The applications of the in vitro synthesis templates disclosed herein may be described by analyzing the advantages and disadvantages of granules of bioactive glass. See Schepers et al. "Bioactive glass particulate material as a filler for bone lesions," J. Oral Rehabilitation, 8, 435–452 (1991). One of the great advantages of using the glass in the form of granules is that they are presently ready for clinical use, and the in vitro synthesis templates are not. Since both are glass based products, the acceptance in the market of granules may greatly help the future introduction of the templates.

It is worthwhile to note that the template disclosed herein can be made in porous particle form. This enables the templates to be used for filling the many different forms of defects one encounters in surgery. However doing so forgoes one of the significant attributes of the templates, namely that they can come as large rigid structures. This is of great significance in any situation of either trauma or pathology, where bone loss is substantial and where the repair and reconstruction must be attempted with solid blocks to give the necessary rigidity to the structure after surgery. In such situations it is a limitation of granules or particles that they form a paste, since they can be squeezed from the site of delivery.

A second major advantage of in vitro synthesized bone tissue formation on templates made in accordance with the present invention is that they can be implanted into sites with otherwise limited growth potential. Cells which have been seeded onto the template in accordance with the methods of the present invention have been made active before implantation. This observation opens up enormous perspectives. Our Western populations are growing ever older and it is in this older age group that osteoporosis is prevalent. Osteoporosis, characterized by greater bone resorption than formation, afflicts more than fifty percent of the population beyond fifty-five years of age. It leads to the gradual compression of the spine and the typical hunch back. Osteoporosis is also the basis of a large percentage of hip fractures, with their considerable morbidity, and even significant secondary mortality. In short, the seeded glass surfaces with in vitro grown bone tissue disclosed herein can be inserted in all areas of the body that exhibit an increased risk of fracture and a decreased or even extinct potential for bone tissue formation. The network of porous, bioactive glass of the present invention can be made such that it resembles the porous bone network in the vertebrae of the spine, or the neck of the hip bone.

The cells seeded on to the synthetic substrate disclosed herein are most preferably cells from the patient. In experiments, osteoblasts, i.e., the cell which secretes the bone tissue material, have been used. However, as well known to those of ordinary skill osteoblasts are merely the end stage cell of cells of osteoblastic lineage. It is also possible, to use cells which are precursor cells to osteoblasts, that are typically present in the bone marrow. A simple extraction, followed by an appropriate separation and conditioning, yields cells that can be seeded. Intra-family donation of these cells are planned for those cases where either the aging of the patient to be treated has progressed to the point where he has only a limited cell activity anymore, or where the clinical circumstances are such that cell biopsies cannot be obtained.

A third important advantage of the porous bioactive glass templates disclosed herein is that they can be implanted in sites where there is an immediate need for bone. Once the templates have been seeded, results indicate that bone tissue has already formed extensively in vitro after one week.

In summary, the present templates will not fully replace the nonporous granules discussed in the Schepers reference noted above, rather they will broaden the indications for which these granules were used before in a rather restrictive way. Furthermore, they will create totally new therapies, such as the ones in osteoporotic pathology as suggested above.

Those of skill in the art will recognize that these porous templates will also become used in primary joint replacements. A porous coated prosthesis will be surrounded by a sleeve of the porous template material made in accordance with the present invention, and seeded with cells. After about one to two weeks, it will be inserted into the patient. At that time, a very expeditious incorporation of the device into the native femoral bone will occur.

Another new and useful area to which the present invention can be applied is the delivery of drugs or biological molecules to a patient. By adding a drug or biological molecules to the substrate, other therapeutic effects in addition to bone replacement can be achieved.

Although certain embodiments and applications of the present invention have been set forth with particularity, review of the foregoing specification will lead those of ordinary skill to realize that the present invention is not so limited. Numerous variations, modifications and application to other indications will immediately become apparent that do not depart from the spirit of the invention. For this reason, reference should be made to the appended claims in order to ascertain the true scope of the present invention.

What is claimed is:

1. A porous bioactive substrate comprising a glass having the following composition: 40–60% by weight $SiO_2$; 10–35% by weight CaO; 5–30% by weight $Na_2O$; and 0–12% by weight $P_2O_5$, said substrate having a porosity of from about 10 to about 80% and a pore size of less than about 800 µm, and substantially no crystallization.

2. The substrate of claim 1 wherein porosity is from about 20 to about 30%.

3. The substrate of claim 1 wherein the pore size is in the range of from about 75 to about 200 µm.

4. The substrate of claim 1 wherein the glass has the following composition: 45% by weight $SiO_2$; 24.5% by weight CaO; 24.5% by weight $Na_2O$; and 6% by weight $P_2O_5$.

5. A porous bioactive substrate comprising a glass consisting essentially of: 40–60% by weight $SiO_2$; 10–35% by weight CaO; 5–30% by weight $Na_2O$; and 0–12% by weight $P_2O_5$, said substrate having a porosity of from about 10 to about 80% and a pore size of less than about 800 µm, wherein said substrate is prepared by the process comprising the steps of:

a) melting an admixture consisting essentially of $SiO_2$, $Na_2O$, CaO, and $P_2O_5$;

b) quenching the melted admixture to create a glass frit;

c) forming a glass powder from the glass frit; and d) forming a porous glass substrate from the glass powder, whereby the resulting porous glass exhibits substantially no crystallization.

* * * * *